United States Patent
Osborne et al.

(10) Patent No.: US 8,809,491 B2
(45) Date of Patent: Aug. 19, 2014

(54) DEPOLYMERIZATION OF OLIGOMERIC CYCLIC ETHERS

(75) Inventors: Robert B. Osborne, Wilmington, DE (US); Paul S. Pearlman, Thornton, PA (US); Yanhui Sun, Wilmington, DE (US)

(73) Assignee: INVISTA North America S.à r.l., Wilmington, DE (US)

( * ) Notice: Subject to any disclaimer, the term of this patent is extended or adjusted under 35 U.S.C. 154(b) by 33 days.

(21) Appl. No.: 13/514,786

(22) PCT Filed: Dec. 11, 2009

(86) PCT No.: PCT/US2009/067691
§ 371 (c)(1),
(2), (4) Date: Aug. 6, 2012

(87) PCT Pub. No.: WO2011/071503
PCT Pub. Date: Jun. 16, 2011

(65) Prior Publication Data
US 2013/0053583 A1 Feb. 28, 2013

(51) Int. Cl.
*C08F 6/00* (2006.01)
*C08G 65/20* (2006.01)
*C07D 307/08* (2006.01)
*C08G 65/32* (2006.01)

(52) U.S. Cl.
CPC .............. *C07D 307/08* (2013.01); *C08G 65/20* (2013.01); *C08G 2650/12* (2013.01); *C08G 2650/34* (2013.01); *C08G 65/32* (2013.01); *C08G 2650/10* (2013.01)
USPC ............. 528/487; 528/480; 528/503; 521/40; 549/429

(58) Field of Classification Search
CPC .... C07D 307/00; C07D 307/08; C08G 65/20; C08G 65/30; C08G 65/32; C08G 2650/10; C08G 2650/12
USPC ................. 528/480, 487, 489, 491, 495, 503; 521/40; 549/429
See application file for complete search history.

(56) References Cited

U.S. PATENT DOCUMENTS

| | | | |
|---|---|---|---|
| 3,282,875 A | 11/1966 | Connolly et al. | |
| 3,308,069 A | 3/1967 | Wadlinger et al. | |
| 3,702,886 A | 11/1972 | Argauer et al. | |
| 3,925,484 A | 12/1975 | Baker | |
| 4,115,408 A * | 9/1978 | Baker | 549/429 |
| 4,120,903 A | 10/1978 | Pruckmayr et al. | |
| 4,139,567 A | 2/1979 | Pruckmayr | |
| 4,153,786 A | 5/1979 | Pruckmayr | |
| 4,163,115 A | 7/1979 | Heinsohn et al. | |
| 4,189,566 A | 2/1980 | Mueller et al. | |
| 4,202,964 A * | 5/1980 | Pruckmayr et al. | 528/482 |
| 4,363,924 A | 12/1982 | Mueller et al. | |
| 4,439,409 A | 3/1984 | Puppe et al. | |
| 4,803,299 A | 2/1989 | Mueller | |
| 4,806,658 A | 2/1989 | Chang et al. | |
| 4,826,667 A | 5/1989 | Zones et al. | |
| 4,954,325 A | 9/1990 | Rubin et al. | |
| 5,118,869 A | 6/1992 | Dorai et al. | |
| 5,149,862 A | 9/1992 | Dorai et al. | |
| 5,236,575 A | 8/1993 | Bennett et al. | |
| 5,250,277 A | 10/1993 | Kresge et al. | |
| 5,362,697 A | 11/1994 | Fung et al. | |
| 5,635,585 A | 6/1997 | Drysdale et al. | |
| 5,773,648 A | 6/1998 | Becker et al. | |
| 6,111,147 A | 8/2000 | Sigwart et al. | |
| 6,197,979 B1 | 3/2001 | Becker et al. | |
| 6,211,401 B1 | 4/2001 | Eller et al. | |
| 6,403,842 B1 | 6/2002 | Kobayashi et al. | |
| 6,429,321 B1 | 8/2002 | Lin et al. | |
| 6,987,201 B2 | 1/2006 | Nishioka et al. | |

FOREIGN PATENT DOCUMENTS

| | | |
|---|---|---|
| DE | 4410685 A1 | 10/1995 |
| DE | 4433606 A | 3/1996 |
| DE | 19641481 | 4/1998 |
| DE | 19649803 | 7/1998 |
| EP | 492807 | 7/1992 |
| JP | 60-109584 | 6/1985 |
| JP | 61-115935 | 6/1986 |
| JP | 61-120832 | 6/1986 |
| JP | 62-257931 | 11/1987 |
| JP | 11-269262 | 10/1999 |
| WO | 94/09055 | 4/1994 |
| WO | 95/02625 | 1/1995 |

OTHER PUBLICATIONS

International Search Report issued in a corresponding patent application PCT/US2009/067691 on Mar. 10, 2010.
Supplementary European Search Report issued in a corresponding patent application EP09852141 on Apr. 3, 2013.

* cited by examiner

*Primary Examiner* — Frances Tischler
(74) *Attorney, Agent, or Firm* — Robert B. Furr, Jr.

(57) ABSTRACT

The present invention provides a method for depolymerization of a mixture comprising oligomeric cyclic ethers resulting from copolymerization of at least one tetrahydrofuran and at least one other cyclic ether to recover tetrahydrofuran monomer.

26 Claims, No Drawings

DEPOLYMERIZATION OF OLIGOMERIC CYCLIC ETHERS

CROSS-REFERENCE TO RELATED APPLICATIONS

This application is related to applications filed concurrently on Dec. 11, 2009 as PCT Application Numbers PCT/US2009/067680, PCT/US2009/067688 and PCT/US2009/067702.

FIELD OF THE INVENTION

The present invention relates to an improved method for depolymerization of a mixture comprising oligomeric cyclic ethers to prepare lower molecular weight reaction products such as tetrahydrofuran. More particularly, the invention relates to a method for depolymerization of a mixture comprising oligomeric cyclic ethers over a particular acid catalyst at depolymerization reaction conditions to yield a reaction product comprising mainly tetrahydrofuran. Still more particularly, the invention relates to a method for depolymerization of a mixture comprising oligomeric cyclic ethers over a particular acid catalyst at depolymerization reaction conditions in the presence of an effective amount of specific depolymerization reaction enhancing additive to yield a reaction product comprising tetrahydrofuran, recovery of the tetrahydrofuran from the reaction product, and purification of the recovered tetrahydrofuran. The invention also relates to a method for depolymerization of a mixture comprising oligomeric cyclic ethers over a particular acid catalyst at depolymerization reaction conditions in the presence of an effective amount of specific depolymerization reaction enhancing additive to increase depolymerization rate.

BACKGROUND OF THE INVENTION

Copolymers of tetrahydrofuran (THF) and at least one other cyclic ether, also known as copolyether glycols, are known for use as soft segments in polyurethanes and other elastomers, particularly where reduced crystallinity imparted by the cyclic ether may improve certain dynamic properties of polyurethane and other elastomers which contain such a copolymer as a soft segment. Examples of cyclic ethers used for this purpose are ethylene oxide and propylene oxide.

The copolymers of THF and at least one other cyclic ether are well known in the art. Their preparation is disclosed, for example, by Heinsohn et. al. in U.S. Pat. No. 4,163,115, by Pruckmayr in U.S. Pat. Nos. 4,120,903 and 4,139,567, and U.S. Pat. No. 4,153,786. Such copolymers can be prepared by any of the known methods of cyclic ether polymerization, described for instance in "Polytetrahydrofuran" by P. Dreyfuss (Gordon & Breach, N.Y. 1982). Such polymerization methods include catalysis by strong proton or Lewis acids, by heteropoly acids, as well as by perfluorosulfonic acids or acid resins. In some instances it may be advantageous to use a polymerization promoter, such as a carboxylic acid anhydride, as disclosed in U.S. Pat. No. 4,163,115. In these cases the primary polymer products are diesters, which need to be hydrolyzed in a subsequent step to obtain polyether glycols.

In these processes, crude product mixtures will contain byproduct oligomeric cyclic ethers of ethylene oxide and tetramethylene oxide units with molecular weight from about 188 to 500 (OCE), which are relatively stable compounds. When feedstock to such processes comprise THF and ethylene oxide, yield of OCE ranges, for example, from about 5 to about 25 wt % depending on the ethylene oxide to THF feedstock ratio. If the conditions are right in such processes conducted in the presence of acid catalysts, some depolymerization occurs, but at very slow rates unless appropriate catalyst and sufficient heat is applied. In any event, when such depolymerization progresses, higher molecular weight copolyether forms with higher viscosity leading to the formation of tars. For example, U.S. Pat. No. 4,202,964 shows that the OCE content of a copolymer product can be reduced by contacting the product with cationic exchange resin at certain conditions. A serious disadvantage to such a method is that open glycol chains in the copolymer product are deoligomerized with significant impact on product molecular weight distribution.

A depolymerization mechanism is shown in, for example, U.S. Pat. No. 6,429,321 where a mixture containing polytetrahydrofuran derivative is depolymerized at increased temperature over catalyst comprising zeolite Beta. Another such process mechanism is shown in U.S. Pat. No. 3,925,484 where polytetramethylene ether glycol (PTMEG) is said to be depolymerized at elevated temperature over cross-linked acid form ion exchange resin. U.S. Pat. No. 4,115,408 shows a process for depolymerizing PTMEG in which effluent containing same is heated with sulfuric acid at high temperature. U.S. Pat. No. 4,363,924 shows use of a bleaching earth as catalyst for such a process at elevated temperature. U.S. Pat. No. 4,806,658 shows that polyethylene glycol can be hydrolyzed into ethylene glycol and its derivatives in the presence of metal oxide catalyst at high temperatures of from 170 to 320° C. Japan Pat. No. 60-109584 shows use of heteropoly acid as catalyst to depolymerize PTMEG. Japan 62-257931 shows use of non-crystalline silica-alumina as catalyst for depolymerization of linear or cyclic PTMEG at elevated temperature. Japan Pat. No. 11-269262 relates to a process where PTMEG is depolymerized over a mixture of zirconia and silica as catalyst.

Japan Pat. No. 61-11593 shows a method for depolymerization of cyclic PTMEG at elevated temperature over silicotungstic acid catalyst. WO No. 95/02625 shows use of metal perfluoroalkanesulfonates, for example $(CF_3SO_3)_3Y$, as catalyst in the presence of an accelerator for a depolymerization mechanism. A distinct commercial disadvantage for this process is the high cost of the catalyst. Germany Pat. No. DE 4410685 shows depolymerizing PTMEG at elevated temperature over catalyst of kaolin, amorphous silica and/or zeolite X.

Pretreatment methods for THF to make same more useful as a polymerization feed include those shown in U.S. Pat. No. 4,189,566 where THF is treated with strong mineral acid, organosulfonic acid, silica gel or a bleaching earth; U.S. Pat. No. 4,803,299 where THF is fractionally distilled; and U.S. Pat. Nos. 6,403,842 and 6,987,201 THF polymerization color improvement focuses on purification of the carboxylic acid anhydride component.

None of the above publications show depolymerization of OCE resulting from copolymerization of THF and at least one other cyclic ether, which are very stable and more difficult to depolymerize than PTMEG. None of the above publications show a method for depolymerization of a mixture comprising OCE over a particular acid catalyst at suitable depolymerization reaction conditions including temperature and contact time in the presence of a specific depolymerization reaction enhancing additive to yield a reaction product comprising tetrahydrofuran. None of the above publications show a method for depolymerization of a mixture comprising OCE including steps to purify the depolymerization product producing high quality THF for PTMEG and its copolymer production.

SUMMARY OF THE INVENTION

The present invention provides a simple economical method for depolymerization of an OCE mixture resulting from copolymerization of THF and at least one other cyclic ether. The method comprises (1) isolating a mixture comprising OCE resulting from copolymerization of THF and at least one other cyclic ether, for example an alkylene oxide, (2) contacting the mixture of step (1) with a particular catalyst, hereinafter more particularly described, at depolymerization reaction conditions, hereinafter more particularly described, optionally in the presence of an effective amount of a specific depolymerization reaction enhancing additive, hereinafter more particularly described, and (3) recovering from step (2) a depolymerization reaction product stream comprising THF (THF stream). The method may further comprise purifying the THF of the THF stream by (4) neutralizing the THF stream of step (3), (5) separating the neutralized THF stream from any salts formed during step (4), (6) distilling the separated neutralized THF stream of step (5) to form a distilled THF-enriched stream, (7) optionally drying the THF-enriched stream from step (6), and (8) removing any residual ethanol generated in the depolymerization process from the THF-enriched stream from step (6) or (7) to result in a purified THF.

The mixture comprising OCE resulting from copolymerization of THF and at least one other cyclic ether may be obtained in any way, such as being isolated as a process stream from a polymerization reaction process, being secured as an off-quality product from such a process, or the like. The product stream comprising THF (THF stream) or recovered purified THF can be recycled, if desired, as feedstock to a THF polymerization reaction process leading to enhanced commercial efficiency for said process.

It is an object of the present invention to provide a simple, commercially economic method for depolymerization of highly stable OCE resulting from copolymerization of THF and at least one other cyclic ether in high yield to recover high value THF monomer, for use as recycle if desired.

DETAILED DESCRIPTION OF THE INVENTION

Disclosed is a method for depolymerization of OCE mixtures resulting from copolymerization of THF and at least one other cyclic ether, said process being simple and commercially economic. The present method may avoid significant high viscosity tar formation or product molecular weight distribution increase and may provide commercially acceptable yield of a useful depolymerization reaction product. An embodiment of the method of the present invention comprises isolating a mixture comprising OCE resulting from copolymerization of THF and at least one other cyclic ether, for example an alkylene oxide, contacting the isolated mixture with a particular catalyst, hereinafter more particularly described, at depolymerization reaction conditions, hereinafter more particularly described, optionally in the presence of an effective amount of a specific depolymerization reaction enhancing additive, hereinafter more particularly described, and recovering a depolymerization reaction product comprising THF (THF stream). The polymerization process resulting in the source for the isolated OCE feedstock for the present method can be any of the known processes for copolymerization of THF and at least one other cyclic ether, for example an alkylene oxide. Another embodiment of the present invention comprises further purifying the THF of the THF stream by neutralizing the THF stream, separating the neutralized THF stream from any salts formed during neutralization, distilling the separated neutralized THF stream of to form a distilled THF-enriched stream, optionally drying the THF-enriched stream to remove any residual water and any residual ethanol byproduct from the THF-enriched stream to result in a purified THF.

The term "polymerization", as used herein, unless otherwise indicated, includes the term "copolymerization" within its meaning.

The term "PTMEG", as used herein, unless otherwise indicated, means polytetramethylene glycol. PTMEG is the generic designation of INVISTA Terathane® polyether glycol.

The term "copolyether glycol", as used herein in the singular, unless otherwise indicated, means copolymers of tetrahydrofuran and at least one other cyclic ether such as 1,2-alkylene oxide, which are also known as polyoxybutylene polyoxyalkylene glycols. An example of a copolyether glycol is a copolymer of tetrahydrofuran and ethylene oxide. This copolyether glycol is also known as poly(tetramethylene-co-ethyleneether) glycol.

The term "THF", as used herein, unless otherwise indicated, means tetrahydrofuran and includes within its meaning alkyl substituted tetrahydrofuran capable of copolymerizing with THF, for example 2-methyltetrahydrofuran, 3-methyltetrahydrofuran, and 3-ethyltetrahydrofuran.

The term "alkylene oxide", as used herein, unless otherwise indicated, means a compound containing two, three or four carbon atoms in its alkylene oxide ring. The alkylene oxide can be unsubstituted or substituted with, for example, linear or branched alkyl of 1 to 6 carbon atoms, or aryl which is unsubstituted or substituted by alkyl and/or alkoxy of 1 or 2 carbon atoms, or halogen atoms such as chlorine or fluorine. Examples of such compounds include ethylene oxide; 1,2-propylene oxide; 1,3-propylene oxide; 1,2-butylene oxide; 1,3-butylene oxide; 2,3-butylene oxide; styrene oxide; 2,2-bis-chloro-methyl-1,3-propylene oxide; epichlorohydrin; perfluoroalkyl oxiranes, for example (1H,1H-perfluoropentyl) oxirane; and combinations thereof.

An embodiment of the present invention comprises a depolymerization method for preparing commercially useful THF. The method involves depolymerization of a mixture comprising OCE which comprises the steps of (1) isolating a mixture comprising OCE resulting from copolymerization of THF and at least one other cyclic ether, for example an alkylene oxide, (2) contacting the isolated mixture of step (1) at depolymerization reaction conditions including a temperature of from about 125° C. to about 200° C., for example from about 135° C. to about 180° C., with catalyst selected from the group consisting of homogeneous and heterogeneous acid catalysts and combinations thereof, for example inorganic acid, e.g., sulfuric acid, soluble in the mixture comprising OCE at depolymerization reaction conditions, zeolite optionally activated by acid treatment, acidic ion-exchange resin, sheet silicate optionally activated by acid treatment, sulfate-doped zirconium dioxide, supported catalyst comprising at least one catalytically active oxygen-containing molybdenum and/or tungsten compound or a mixture of such compounds applied to an oxidic support, polymeric catalyst which contains sulfonic acid groups, and combinations thereof, optionally in the presence of an effective amount of a depolymerization reaction enhancing additive selected from the group consisting of $C_2$-$C_8$ alcohols, $C_2$-$C_{10}$ diols, polytetramethylene glycol, $C_2$-$C_{12}$ carboxylic acids, and combinations thereof, to yield a depolymerization reaction product stream comprising THF, and (3) recovering the depolymerization reaction product stream comprising THF of step (2) (the THF stream).

Another embodiment of the present invention comprises the steps of (1) isolating a mixture comprising from about 40 to about 100 wt % OCE resulting from copolymerization of THF and at least one alkylene oxide, for example ethylene oxide, (2) contacting the isolated mixture of step (1) at depolymerization reaction conditions including a temperature of from about 125° C. to about 200° C., for example from about 135° C. to about 180° C., and contact time from about 0.5 to about 15 hours, for example from about 2 to about 15 hours, with catalyst selected from the group consisting of homogeneous and heterogeneous acid catalysts and combinations thereof, for example inorganic acid, e.g., sulfuric acid, soluble in the mixture comprising OCE at depolymerization reaction conditions, polymeric catalyst which contains sulfonic acid groups and combinations thereof, optionally in the presence of an effective amount of a depolymerization reaction enhancing additive selected from the group consisting of heptanol, octanol, ethylene glycol, propylene glycol, butane diol, pentane diol, polytetramethylene glycol, propionic acid, butyric acid, valeric acid and combinations thereof, to yield a depolymerization reaction product stream comprising THF, and (3) recovering the depolymerization reaction product stream comprising THF of step (2) (the THF stream).

The alkylene oxide in step (1) may comprise, for example, ethylene oxide or propylene oxide. The depolymerization reaction conditions of step (2) include, for example, a temperature of from about 125° C. to about 200° C. and contact time from about 2 to about 15 hours, e.g., from about 2 to about 8 hours. The contacting of step (2) may be in a stainless steel vessel, and the mixture in said vessel may be agitated, for example by shaking or mixing, for example at from about 60 to about 400 rpm. The pressure in the vessel is not narrowly critical and may be maintained at atmospheric pressure, the autogenous pressure of the step (2) contacting, or elevated pressure.

Another embodiment of the present invention comprises further purifying the THF of the THF stream of step (3) by (4) neutralizing the THF stream, (5) separating the neutralized THF stream from any salts formed during step (4), (6) distilling the separated neutralized THF stream of step (5) to form a distilled THF-enriched stream, (7) optionally drying the THF-enriched stream from step (6), and (8) removing any residual ethanol from the THF-enriched stream from step (6) or (7) to result in a purified THF.

Isolating a mixture comprising OCE resulting from copolymerization of THF and at least one other cyclic ether, for example an alkylene oxide, may be accomplished by any suitable means. One such method involves distillation, e.g., short path distillation, of the crude product from the copolymerization reactor after first removing unreacted starting materials and other monomeric reaction products by simple stripping operations. Another example of a suitable method is solvent extraction. This step provides a suitable feedstock to the present method without affecting the desired copolymerization product, such as a copolyether glycol.

The catalysts for use in step (2) of the present method include inorganic acids which are soluble in the mixture comprising OCE at depolymerization reaction conditions, zeolites optionally activated by acid treatment, acidic ion-exchange resins, sheet silicates optionally activated by acid treatment, sulfate-doped zirconium dioxide, supported catalysts comprising at least one catalytically active oxygen-containing molybdenum and/or tungsten compound or a mixture of such compounds applied to an oxidic support, polymeric catalysts which contain sulfonic acid groups and combinations thereof.

Among the inorganic acids useful as catalyst herein are sulfuric acid and other strong mineral acids. Such acid catalysts must remain soluble in the mixture comprising OCE at depolymerization reaction conditions.

Among the zeolites for use as catalyst herein are natural or synthetic zeolites, a class of aluminum hydrosilicates (also known as crystalline aluminosilicates), having an open structure of three-dimensional networks with defined pores and channels in the crystal. Suitable zeolites for use herein have a $SiO_2:Al_2O_3$ molar ratio ranging from about 4:1 to about 100:1, for example from about 6:1 to about 90:1, or from about 10:1 to about 80:1. The particle size of the zeolite may be less than about 0.5 micron, for example less than about 0.1 micron, or less than about 0.05 micron. The zeolites are used in the hydrogen (acid) form and may optionally be activated by acid treatment. The acidified zeolites for use herein are exemplified by faujasite (described in EP-A 492807), zeolite Y, zeolite Beta (described in U.S. Pat. No. 3,308,069), ZSM-5 (described in U.S. Pat. No. 3,702,886), MCM-22 (described in U.S. Pat. No. 4,954,325), MCM-36 (described in U.S. Pat. No. 5,250,277), MCM-49 (described in U.S. Pat. No. 5,236,575), MCM-56 (described in U.S. Pat. No. 5,362,697), PSH-3 (described in U.S. Pat. No. 4,439,409), SSZ-25 (described in U.S. Pat. No. 4,826,667) and the like.

Among the sheet silicates, optionally activated by acid treatment, which may be used herein as catalyst are disclosed, for example, in U.S. Pat. No. 6,197,979. Examples of suitable sheet silicates for use herein include those of the montmorillonite/saponite, kaolin/serpentine, or polygorskite/sepiolite groups, for example montmorillonite, hectorite, kaolin, attapulgite, or sepiolite.

The preparation of sulfate-doped zirconium dioxide, which may be used as catalyst herein, is disclosed, for example, in U.S. Pat. No. 5,149,862.

Also useful as catalysts herein are those comprising at least one catalytically active oxygen-containing molybdenum and/or tungsten compound or a mixture of such compounds applied to an oxidic support as disclosed, for example, in U.S. Pat. No. 6,197,979. Examples of suitable oxidic supports include zirconium dioxide, titanium dioxide, hafnium oxide, yttrium oxide, iron (III) oxide, aluminum oxide, tin (IV) oxide, silicon dioxide, zinc oxide or mixture of these oxides. The supported catalysts may be, for example, additionally doped with sulfate or phosphate groups, as disclosed in German patent application DE-A 44 33606, pretreated with a reducing agent as described in DE 196 41481, or calcined and further comprising a promoter comprising at least one element or compound of an element of groups 2, 3 (including the lanthanides), 5, 6, 7, 8, and 14 of the periodic table of the elements, as disclosed in DE 196 49803.

Among the suitable polymeric catalysts which contain sulfonic acid groups which may be used the present invention, optionally with or without carboxylic acid groups, are those whose polymer chains are copolymers of tetrafluoroethylene or chlorotrifluoroethylene and a perfluoroalkyl vinyl ether containing sulfonic acid group precursors (again with or without carboxylic acid groups) as disclosed in U.S. Pat. Nos. 4,163,115 and 5,118,869, and as supplied commercially by E. I. du Pont de Nemours and Company under the trade name Nafion®. Such polymeric catalysts are also referred to as polymers comprising alpha-fluorosulfonic acids. An example of this type of catalyst for use herein is a perfluorosulfonic acid resin, i.e. it comprises a perfluorocarbon backbone and the side chain is represented by the formula $-O-CF_2CF(CF_3)-O-CF_2CF_2SO_3H$. Polymers of this type are disclosed in U.S. Pat. No. 3,282,875 and can be made by copolymerization of tetrafluoroethylene (TFE) and the perfluorinated vinyl ether $CF_2$=CF—O—$CF_2CF(CF_3)$—O—$CF_2CF_2SO_2F$, perfluoro (3,6-dioxa-4-methyl-7-octene-sulfonyl fluoride) (PDMOF), followed by conversion to sulfonate groups by hydrolysis of the sulfonyl fluoride groups and ion exchanged as necessary to convert them to the desired acidic form.

The catalysts which can be employed according to the present invention can be used in the form of powders or as shaped bodies, for example in the form of beads, cylindrical extrudates, spheres, rings, spirals, or granules.

The depolymerization reaction enhancing additive for use in the present invention is selected from the group consisting of $C_2$-$C_8$ alcohols, $C_2$-$C_{10}$ diols, polytetramethylene glycol, $C_2$-$C_{12}$ carboxylic acids, and combinations thereof. Examples of the alcohols for use as the additive include heptanol, octanol or a combination thereof. Examples of the diols for use as the additive include ethylene glycol, propylene glycol, butane diol, pentane diol or a combination thereof. Examples of the carboxylic acids for use as the additive include acetic acid, propionic acid, butyric acid, valeric acid or a combination thereof. An effective amount of the additive in the mixture in step (2) is from about 2 to about 80 mol %, for example from about 2 to about 70 mol %, e.g., from about 2 to about 30 mol % of the mixture.

The process of the invention can be carried out continuously, or with steps of the process being carried out batchwise.

Step (2) of the present method can be carried out in conventional vessel assemblies suitable for continuous processes in a suspension or fixed-bed mode, for example in loop reactors or stirred reactors in the case of a suspension process or in tube reactors or fixed-bed reactors in the case of a fixed-bed process. A continually stirred tank reactor (CSTR) is useful due to the need for good mixing in the present depolymerization method step (2), especially when the depolymerization reaction product comprising THF is produced in a single pass mode.

In a fixed-bed reaction vessel, the depolymerization reactor apparatus can be operated in the upflow mode, that is, the reaction mixture is conveyed from the bottom upward, or in the downflow mode, that is, the reaction mixture is conveyed through the reactor from the top downward.

The depolymerization method step (2) can be conducted using a single pass without internal recirculation of depolymerization reaction product, such as in a CSTR.

Feed mixture can be introduced to the depolymerization vessel using delivery systems common in current engineering practice either batchwise or continuously.

The THF of the depolymerization reaction product stream of step (3) or the further purified THF of step (8) can be recovered by recovery systems and methods common in current engineering practice. Such systems and methods include, as non-limiting examples, neutralization with alkali hydroxide solids or solutions and separation of those solids in a decantation device or by distillation, distillation of a purified wet THF stream on a batch or a continuous column, and removal of ethanol from distillate by appropriate molecular sieves. The recovered depolymerization reaction product stream of step (3) may comprise, for example, from about 70 to about 99 wt % tetrahydrofuran.

The neutralization step (4) may be accomplished by means common in current engineering practice, including stirring the recovered depolymerization reaction product stream, the THF stream, with alkali hydroxide solids or solutions, or passing the recovered depolymerization reaction product stream, the THF stream, through a column containing a basic material.

The separation step (5) may be accomplished by means common in current engineering practice, including decantation of trace solids from the neutralized depolymerization reaction product stream or overhead removal of THF solution from the solids.

The distillation step (6) may be accomplished by means common in current engineering practice, including feeding the separated neutralized stream of step (5) to the side of a distillation column and taking off a side stream and high boilers from the column heel, while maintaining a feed rate and column profiles designed to optimize THF purity and yield, thereby forming a distilled tetrahydrofuran-enriched stream.

The optional drying step (7) to remove residual water, if desired, may be accomplished by means common in current engineering practice, including drying the stream with molecular sieves or running the wet THF stream through an azeotropic distillation column followed by a pressure column to break the THF/water azeotrope composition and yield a dry THF stream.

The residual ethanol removal step (8) may be accomplished by means common in current engineering practice, including passing the dried THF stream over a molecular sieve bed activated for ethanol removal.

The following Examples demonstrate the present invention and its capability for use. The invention is capable of other and different embodiments, and its several details are capable of modifications in various apparent respects, without departing from the spirit and scope of the present invention. Accordingly, the Examples are to be regarded as illustrative in nature and not as restrictive.

Materials

The OCE is obtained from INVISTA S.à r.l., and is isolated by short path distillation from a product of copolymerization of THF and ethylene oxide. The perfluorinated sulfonic acid resin, NR50 Nafion®, is obtained from E. I. du Pont de Nemours, Wilmington, Del., USA. The PTMEG (Terathane®) is obtained from INVISTA S.à r.l. The Amberlyst®15 ion-exchange resin is obtained from Aldrich Chemicals.

Analytical Methods

An NMR spectrometer is used to determine compositions of OCE and linear copolyether. A GC method is used to analyze the overhead distillates, i.e. the depolymerization reaction product.

EXAMPLES

All parts and percentages are by weight unless otherwise indicated.

Example 1

A 250 mL flask equipped with a stirrer, distillation take-off receiver and a thermal couple is charged with 75 parts OCE, 72 parts butanediol depolymerization reaction enhancing additive, and 7.52 parts 98% sulfuric acid (5 wt %) catalyst. The resulting mixture is heated to 135° C. under nitrogen protection while stirring at 350 rpm for 2.5 hours. Analysis of the resulting depolymerization reaction product indicated that 97% THF monomer is recovered from the starting OCE.

Example 2

A 250 mL flask equipped with a stirrer, distillation take-off receiver and a thermal couple is charged with 154 parts OCE, 72 parts butyric acid depolymerization reaction enhancing additive, and 7.523 parts 98% sulfuric acid (5 wt %) catalyst. The mixture is heated to 135° C. under nitrogen protection while stirring at 350 rpm for 8 hours. Analysis of the resulting depolymerization reaction product indicates that 95% THF is recovered from the starting OCE. The depolymerization product contains about 23% dioxane.

Example 3

The experiment of Example 2 is repeated, except that 155 parts OCE, 7.91 parts 98% sulfuric acid (5 wt %) catalyst and no depolymerization reaction enhancing additive is used, and the reaction time is 12 hours. Analysis of the resulting depolymerization reaction product indicates that 90% THF is recovered from the starting OCE. The depolymerization product contains about 20% dioxane.

Example 4

A 500 mL flask equipped with a stirrer, thermocouple and distillation take-off receiver is charged with 12.6 parts Nafion® catalyst, and 237.8 parts OCE mixture isolated from an ethylene oxide-THF copolymerization product by short path distillation. This mixture is heated to an average temperature of 132° C. over a 4 hour period while overhead distillate is collected. The flask reactor is sampled hourly. Rapid OCE decay to 0.8% residual after 4 hours is observed (99% OCE degradation). The recovered overhead stream comprises 96.4% THF and 2.7% dioxane, representing 40.8% THF and 4.3% yield of THF and dioxane value respectively from the original OCE charge.

Example 5

A 500 mL flask equipped with a stirrer, thermocouple and distillation take-off receiver is charged with 13.1 parts Nafion® catalyst, and 90.1 parts OCE mixture isolated from an ethylene oxide-THF copolymerization product by short path distillation. This mixture is heated to an average temperature of 149.3° C. over a 4 hour period, while at the same time 200.0 parts additional OCE is added to the ongoing reaction by an addition funnel. Overall catalyst per total OCE reacted is 4.9% while overhead distillate is collected. The flask reactor is sampled hourly. The recovered overhead stream comprises 87.7% THF, 10.4% dioxane and 1.9% impurities, representing 56.8% THF and 25.1% yield of THF and dioxane value respectively from the original OCE charge.

Example 6

A 500 mL flask equipped with a stirrer, thermocouple and distillation take-off receiver is charged with 13.0 parts Amberlyst®15 ion-exchange resin catalyst, and 90.5 parts OCE mixture isolated from an ethylene oxide-THF copolymerization product. This mixture is heated to an average temperature of 141.5° C. over a 4 hour period, while at the same time 200.3 parts additional OCE is added to the ongoing reaction by an addition funnel. Overall catalyst per total OCE reacted is 4.8%. Overhead distillate is collected. The flask reactor is sampled hourly. The recovered overhead stream comprises 90.9% THF, 6.7% dioxane and 2.4% impurities, representing 49.6% THF and 13.5% yield of THF and dioxane value respectively from the original OCE charge.

Examples 7-16

Ten experiments are conducted in the 250 mL flask reactor used for Examples 1 and 2, with 154 parts OCE, 7.523 parts 98% sulfuric acid catalyst, and various amounts in mol % of depolymerization reaction enhancing additive. No additive is added for Example 7 for comparison purposes. The additives, their amounts, reaction times, THF recovery yields and product viscosities are listed in Table I.

TABLE I

| Example | Additive Compound | Additive Amount (mol %) | Reaction Time (minutes) | THF Recovery Yield (%) |
| --- | --- | --- | --- | --- |
| 7 | None | — | 2.5 | 52 |
| 8 | Butanediol | 9.1 | 2.5 | 58 |
| 9 | Butanediol | 30.0 | 2.5 | 67 |
| 10 | Butanediol | 66.7 | 2.5 | 97 |
| 11 | Butanediol | 100 | 0.83 | 97 |
| 12 | PTMEG | 25.0 | 2.5 | 62 |
| 13 | PTMEG | 66.7 | 2.5 | 82 |
| 14 | PTMEG | 100 | 0.78 | 92 |
| 15 | Ethylene Glycol | 9.1 | 2.5 | 59 |
| 16 | Octanol | 9.1 | 2.5 | 57 |

Example 17

A four neck, 500 mL round bottom flask equipped with a stirrer, a five plate Odlershaw column, a distillation receiver and a thermal couple is charged with a reaction mixture containing 300 parts OCE and 6.122 parts 98% sulfuric acid (5 wt %) catalyst. The reaction mixture is heated to 150° C. while stirring at 500 rpm. THF begins distilling off at the overhead and additional feedstock containing 99.5 parts OCE and 0.5 parts sulfuric acid catalyst is added to the flask at about the same rate as the overhead distillation. This continuous depolymerization reaction is run for 294 hours. The OCE depolymerization conversion is greater than 95% with no bottom purge necessary. The bottom residue shows no solid tar formation. The product stream comprises about 80 wt % THF, 18 wt % dioxane, 1.1 wt % water and 0.26 wt % $H_2SO_4$ and other impurities.

Example 18

An 811 part portion of the product stream from Example 17 is mixed with 6.99 parts 50% NaOH solution (100% excess) in a separate vessel and stirred with a magnetic stirrer for 4 hours at 25° C. for neutralization. The solution turns yellow and then orange during the neutralization due to aldol condensation of impurities and reached a pH of 9. The neutralized product is then allowed to stand overnight in order to separate the neutralized THF product from salts formed during neutralization. The separated neutralized THF product is then decanted away from the salts. The decanted neutralized THF product is then distilled by feeding to a 25 tray, six foot column at the fifth tray, taking off THF product as a side draw at the twentieth tray with a 3/1 reflux ratio. The top fraction is collected from the twenty-fifth tray overhead with a 20/1 reflux ratio. The collected THF product comprises 99.8% THF, and 0.008-0.015% ethanol on an organic basis accompanied by a small percentage of water. This product is then passed through a vessel containing 5 A molecular sieve to remove most of the ethanol.

Example 19

A 1008 part portion of the product stream from Example 17 is mixed with 5.0 parts 50% NaOH solution and 13.4 parts $H_2O$ in the reaction vessel used in Example 18. During stirring for 22 hours, the solution turns to an off-white color. With stirring stopped, the solution is decanted from off-white neutralization solids. The decanted neutralized THF product is then distilled by feeding to a 25 tray, six foot column at the fifth tray, taking off THF product as a side draw at the twentieth tray with a 4/1 reflux ratio. The top fraction is collected from the twenty-fifth tray overhead with a 20/1 reflux ratio. The collected THF product comprises 99.8-99.9% THF, and 0.007-0.008% ethanol on an organic basis accompanied by a small percentage of water. This THF product may be used in a polymerization reaction mixture with the residual water useful as molecular weight control agent.

All patents, patent applications, test procedures, priority documents, articles, publications, manuals, and other documents cited herein are fully incorporated by reference to the extent such disclosure is not inconsistent with this invention and for all jurisdictions in which such incorporation is permitted.

When numerical lower limits and numerical upper limits are listed herein, ranges from any lower limit to any upper limit are contemplated.

While the illustrative embodiments of the invention have been described with particularity, it will be understood that various other modifications will be apparent to and may be readily made by those skilled in the art without departing from the spirit and scope of the invention. Accordingly, it is not intended that the scope of the claims hereof be limited to the examples and descriptions set forth herein but rather that the claims be construed as encompassing all the features of patentable novelty which reside in the present invention, including all features which would be treated as equivalents thereof by those skilled in the art to which the invention pertains.

What is claimed:

1. A method for depolymerization of a mixture comprising oligomeric cyclic ether which comprises the steps of (1) isolating a mixture comprising oligomeric cyclic ether resulting from copolymerization of tetrahydrofuran and at least one other cyclic ether, (2) contacting the mixture of step (1) at depolymerization reaction conditions including a temperature of from about 125° C. to about 200° C. with catalyst selected from the group consisting of homogeneous and heterogeneous acid catalysts and combinations thereof, in the presence of an effective amount of a depolymerization reaction enhancing additive selected from the group consisting of $C_2$-$C_8$ alcohols, $C_2$-$C_{10}$ diols, polytetramethylene glycol, $C_2$-$C_{12}$ carboxylic acids, and combinations thereof, to yield a depolymerization reaction product stream comprising tetrahydrofuran, and (3) recovering the depolymerization reaction product stream of step (2).

2. The method of claim 1 wherein the catalyst is selected from the group consisting of inorganic acid soluble in the mixture comprising oligomeric cyclic ether at depolymerization reaction conditions, zeolite optionally activated by acid treatment, acidic ion-exchange resin, sheet silicate optionally activated by acid treatment, sulfate-doped zirconium dioxide, supported catalyst comprising at least one catalytically active oxygen-containing molybdenum and/or tungsten compound or a mixture of such compounds applied to an oxidic support, polymeric catalyst which contains sulfonic acid groups, and combinations thereof.

3. The method of claim 1 wherein the mixture of step (1) comprises from about 40 to about 100 wt % oligomeric cyclic ether.

4. The method of claim 1 wherein the catalyst of step (2) comprises inorganic acid which is soluble in the mixture comprising oligomeric cyclic ether at depolymerization reaction conditions, polymeric catalyst which contains sulfonic acid groups and combinations thereof.

5. The method of claim 4 wherein the catalyst of step (2) comprises a perfluorosulfonic acid resin.

6. The method of claim 1 wherein the depolymerization reaction conditions of step (2) include a temperature of from about 135° C. to about 180° C. and the contact time is from about 0.5 to about 15 hours.

7. The method of claim 1 wherein the depolymerization reaction enhancing additive is one or a combination of $C_2$-$C_8$ alcohols.

8. The method of claim 7 wherein the depolymerization reaction enhancing additive comprises heptanol, octanol or a combination thereof.

9. The method of claim 1 wherein the depolymerization reaction enhancing additive is one or a combination of $C_2$-$C_{10}$ diols.

10. The method of claim 9 wherein the depolymerization reaction enhancing additive comprises ethylene glycol, propylene glycol, butane diol, pentane diol or a combination thereof.

11. The method of claim 1 wherein the depolymerization reaction enhancing additive is polytetramethylene glycol.

12. The method of claim 1 wherein the depolymerization reaction enhancing additive is one or a combination of $C_2$-$C_{12}$ carboxylic acids.

13. The method of claim 12 wherein the depolymerization reaction enhancing additive comprises propionic acid, butyric acid, valeric acid or a combination thereof.

14. The method of claim 1 wherein the recovered depolymerization reaction product stream of step (3) comprises from about 70 to about 99 wt % tetrahydrofuran.

15. The method of claim 1 wherein the other cyclic ether comprises alkylene oxide.

16. The method of claim 15 wherein the alkylene oxide comprises ethylene oxide.

17. The method of claim 1 further comprising the steps of (4) neutralizing the recovered depolymerization reaction product stream of step (3) to obtain a neutralized depolymerization reaction product stream, (5) separating the neutralized depolymerization reaction product stream from any salts formed during step (4), (6) distilling the separated neutralized stream of step (5) to form a distilled tetrahydrofuran-enriched stream, (7) optionally drying the tetrahydrofuran-enriched stream from step (6), and (8) removing residual ethanol from the tetrahydrofuran-enriched stream from step (6) or (7) to result in purified tetrahydrofuran.

18. A method for depolymerization of a mixture comprising oligomeric cyclic ether which comprises the steps of (1) isolating a mixture comprising from about 40 to about 100 wt % oligomeric cyclic ether resulting from copolymerization of tetrahydrofuran and at least one alkylene oxide, (2) contacting the mixture of step (1) at depolymerization reaction conditions including a temperature of from about 125° C. to about 200° C. with catalyst selected from the group consisting of inorganic acid soluble in the mixture comprising oligomeric cyclic ether at depolymerization reaction conditions, polymeric catalyst which contains sulfonic acid groups and combinations thereof, in the presence of an effective amount of a depolymerization reaction enhancing additive selected from the group consisting of heptanol, octanol, ethylene glycol, propylene glycol, butane diol, pentane diol, polytetramethylene glycol, propionic acid, butyric acid, valeric acid and combinations thereof, to yield a depolymerization reaction product stream comprising tetrahydrofuran, and (3) recovering the depolymerization reaction product stream of step (2).

19. The method of claim 18 wherein the alkylene oxide comprises ethylene oxide.

20. The method of claim 18 wherein the catalyst of step (2) comprises a polymeric catalyst which contains sulfonic acid groups.

21. The method of claim 20 wherein the catalyst of step (2) comprises a perfluorosulfonic acid resin.

22. The method of claim 18 wherein the depolymerization reaction conditions of step (2) include a temperature of from about 135° C. to about 180° C. and the contact time is from about 0.5 to about 15 hours.

23. The method of claim 18 wherein the recovered depolymerization reaction product of step (3) comprises from about 70 to about 99 wt % tetrahydrofuran.

24. The method of claim 18 further comprising the steps of (4) neutralizing the recovered depolymerization reaction product stream of step (3) to obtain a neutralized depolymerization reaction product stream, (5) separating the neutralized depolymerization reaction product stream from any salts formed during step (4), (6) distilling the separated neutralized stream of step (5) to form a distilled tetrahydrofuran-enriched stream, (7) optionally drying the tetrahydrofuran-enriched stream from step (6), and (8) removing residual ethanol from the tetrahydrofuran-enriched stream from step (6) or (7) to result in purified tetrahydrofuran.

25. The method of claim 1 wherein the catalyst of step (2) comprises inorganic acid which is soluble in the mixture comprising oligomeric cyclic ether at depolymerization reaction conditions including a temperature of from about 125° C. to about 200° C., and wherein the recovered depolymerization reaction product stream of step (3) comprises from about 70 to about 99 wt % tetrahydrofuran.

26. The method of claim 25 further comprising the steps of (4) neutralizing the recovered depolymerization reaction product stream of step (3) to obtain a neutralized depolymerization reaction product stream, (5) separating the neutralized depolymerization reaction product stream from any salts formed during step (4), and (6) distilling the separated neutralized stream of step (5) to form a distilled tetrahydrofuran-enriched stream.

* * * * *